United States Patent [19]

Klein et al.

[11] Patent Number: 5,766,908

[45] Date of Patent: Jun. 16, 1998

[54] HIGH-FLUX SEMIPERMEABLE MEMBRANE CONTAINING IMMOBILIZED AFFINITY LIGANDS

[75] Inventors: Elias Klein; Donald H. Yeager, both of Louisville, Ky.

[73] Assignee: Akzo Nobel NV, Arnhem, Netherlands

[21] Appl. No.: 778,689

[22] Filed: Jan. 3, 1997

Related U.S. Application Data

[63] Continuation of Ser. No. 400,883, Mar. 8, 1995, abandoned.

[51] Int. Cl.[6] .................... C12N 11/12; G01N 33/544; C07K 17/06; C07K 17/12

[52] U.S. Cl. .................... 435/179; 435/177; 435/181; 435/815; 436/528; 436/530; 436/532; 530/402; 530/413; 530/812; 530/814; 530/816

[58] Field of Search .................... 435/174, 177, 435/179, 180, 181; 436/528, 529, 530, 532; 530/413, 414, 417, 812, 813, 814, 816

[56] References Cited

U.S. PATENT DOCUMENTS

| | | | |
|---|---|---|---|
| 3,853,708 | 12/1974 | Porath et al. | 195/68 |
| 3,959,080 | 5/1976 | Orth et al. | 195/63 |
| 4,051,300 | 9/1977 | Klein et al. | 428/398 |
| 4,693,985 | 9/1987 | Degen et al. | 436/531 |
| 4,840,819 | 6/1989 | Williams et al. | 427/245 |
| 4,948,836 | 8/1990 | Solomon et al. | 525/54.1 |
| 5,053,133 | 10/1991 | Klein et al. | 40/500.38 |
| 5,232,601 | 8/1993 | Chu et al. | 40/646 |
| 5,451,683 | 9/1995 | Barrett et al. | 548/302.7 |

OTHER PUBLICATIONS

"Specific Conjugation Reactions of the Oligosaccharide Moieties of Immunoglobulins", O'Shannessy et al., *Journal of Applied Biochemistry* 7, pp. 347–355 (1985).

"Strategy for the Immobilization of Monoclonal Antibodies of Solid-Phase Supports", Matson et al., *Journal of Chromatography*, 458, pp. 67–77 (1988).

*Primary Examiner*—David M. Naff
*Attorney, Agent, or Firm*—Hoffman, Wasson & Gitler

[57] ABSTRACT

An affinity support is provided containing a high flux semipermeable hydrogel membrane surface-modified with an affinity ligand, such as a protein which may be an antibody or enzyme, or a cell receptor complement, useful for affinity separation of biological macromolecules, including insoluble proteins, cells, and cell fragments, from solution. The exclusion limit (molecular weight cut-off) of the matrix is selected to substantially restrict immobilized protein or other ligand to the surface thereof for maximization of available ligand binding capacity. The exclusion limit is also selected to permit reagent(s) used for the matrix/ligand linkage to penetrate into and form covalent bonds with the membrane on the interior surfaces of the membrane for optimizing packing densities of the affinity ligand exterior to the membrane. By this substantially complete orientation of affinity ligand between affinity matrix and solution interface, the recognition sites of the proteins or other ligands are maximally available to complementary molecules or cells bearing complementary determinants for complexing therewith.

33 Claims, 1 Drawing Sheet

HIGH-FLUX SEMIPERMEABLE MEMBRANE CONTAINING IMMOBILIZED AFFINITY LIGANDS

This application is a continuation of application Ser. No. 08/400,883 filed on Mar. 8, 1995, now abandoned.

BACKGROUND OF THE INVENTION

The invention relates to an affinity support for affinity chromatography comprising a semipermeable hydrogel membrane affinity matrix supporting highly localized surface concentrations of an affinity ligand oriented outwardly from the matrix surface for maximized binding capacity of the ligand, especially for use in the capture of insoluble biological macromolecules, cells, and cell fragments. The support has particular use in immunoaffinity chromatography.

1. Field of the Invention.

The invention relates to an affinity matrix comprising a high flux semipermeable hydrogel membrane surface-modified with an affinity ligand, especially a protein such as an antibody, antigen, or enzyme, or complement to a cell surface receptor, useful for affinity separation of biological molecules, cells or cell fragments from solution. The exclusion limit (molecular weight cut-off) of the membrane is selected to substantially restrict immobilized protein or other ligand to the outer planar surface of the membrane for maximization of available binding capacity for biological moieties which cannot penetrate the pores of the membrane. The exclusion limit is also selected to permit reagent(s) used for linking ligand to membrane to penetrate into and form linkages with the membrane on the interior pore or channel surfaces thereof for optimizing packing densities of the affinity ligand on the membrane surface (i.e., so that immobilized affinity ligands extend only from the outer planar surface of the membrane and are minimally sterically hindered with bulky linking and/or activating reagents or residues thereof). By limiting orientation of affinity ligand between the matrix and solution interface, combined with unrestricted access of immobilizing reagents to the interior of the membrane, the recognition sites of the ligands are maximally available to large insoluble complementary macromolecules, cells, or cell fragments in the solution which cannot penetrate the pore structure of the membrane.

2. Description of Related Art.

Immobilization of ligands on polymer matrices for affinity chromatography is well-known in the art.

Typically, known matrices comprise supporting polymer hydrogels such as polymers or copolymers of (meth)acrylic acid, (meth)acrylate, (meth)acrylamide, agarose, cellulose, or derivatized cellulose wherein the exclusion limits of the membrane are such that the affinity protein or other ligand can readily penetrate the pore structure of the membrane for immobilization on the interior surfaces thereof. U.S. Pat. No. 4,948,836 to Solomon, for example, describes an acrylamide/acrylate matrix copolymer comprising macroporous beads having channels and voids of a diameter of 1,000–25,000 Å wherein ligates such as enzymes and substrate molecules with a size of 10–100 Å can reach "the entire interior of the macroporous matrix". While soluble enzymes or other ligates and smaller insoluble ligates may be able to access affinity ligands including antibodies or other affinity proteins linked within the interior of such membranes, pore/channel/void diameters of 25,000 Å or even more will exclude larger insoluble biological macromolecules and substantially all formed cell elements. Since a large proportion of the potential ligand binding sites of these supports are accordingly inaccessible to such ligates, capture efficiencies of these matrices for large insoluble biological macromolecules and cell elements are very low and these matrices are consequently not much used in practice for this purpose. Enlargement of membrane pores to accommodate macromolecules or formed cell elements significantly larger than about 25,000 Å is generally not a viable option owing to unacceptable loss of membrane mechanical strength.

Further, known methods for immobilizing proteins or other ligands on affinity membranes have many limitations in practice, especially as concerns the application of these methods to cellulosic membranes. Classic methods include the use of carbonyl diimidazole (CDI) as an activating agent to produce covalent urethane links between various polymer membranes and affinity protein. Since CDI is hydrolyzed rapidly in water, initial membrane activation using this reagent requires the use of an aprotic solvent. For cellulosic and other hydrogel membranes, the aprotic solvent must be capable of preserving the water-swollen state of the membrane without seriously compromising its mechanical strength or affecting its permeability. Dehydration of cellulose by solvent exchange as known in the art for other chromatographic hydrogels using aprotic, water miscible solvents has been accordingly considered (inventors unpublished data). However, the use of common aprotic solvents such as acetone or acetonitrile in conjunction with cellulose fibers under conditions which lead to sufficient dehydration also lead to loss of mechanical (particularly tensile) strength of the membrane and loss of permeability, making it unsuitable for use as a supporting membrane for immobilizing affinity ligand. Further, in the cellulosic membranes studied, the urethane linkages between the cellulose and protein bound the protein so tightly to the membrane surfaces that significant recognition properties of the protein were compromised. Additionally, cellulosic membranes according to the invention are preferably encased in plastic housings prior to protein immobilization to facilitate the above-described-surface-limited reactions. Since many otherwise useful plastics are susceptible to damage by organic solvents, suitable housing materials for use with aprotic solvents are limited.

It is accordingly desirable to provide a mechanically strong high flux affinity matrix for immobilization of affinity ligand having a molecular weight cutoff which substantially restricts the affinity protein to the exterior surface of the membrane while permitting entry of linking/activating reagent(s) into the interior of the membrane. Preferably, the membrane includes a bifunctional spacer molecule or leash covalently linking the membrane and ligand which promotes spacing of the protein or other ligand from the exterior surface of the membrane to substantially exclusively orient the protein or other ligand between the membrane and solution interface for maximization of overall binding capacity of the affinity membrane. Most preferably, the linking reagents are selected for immobilization of affinity protein in an all-aqueous solvent system.

BRIEF DESCRIPTION OF THE DRAWING

In the Drawing, the sole FIGURE is a representational cross-section of a membrane according to the invention illustrating nominal exterior surface(s) 2 of a matrix membrane 1, interior pore/void/channel surfaces (herein referred to as interior pore surfaces) 3 of the membrane 1, and spacer linkages 4 between the membrane 1 and immobilized affinity protein molecules 6.

SUMMARY OF THE DISCLOSURE

Figure 1:
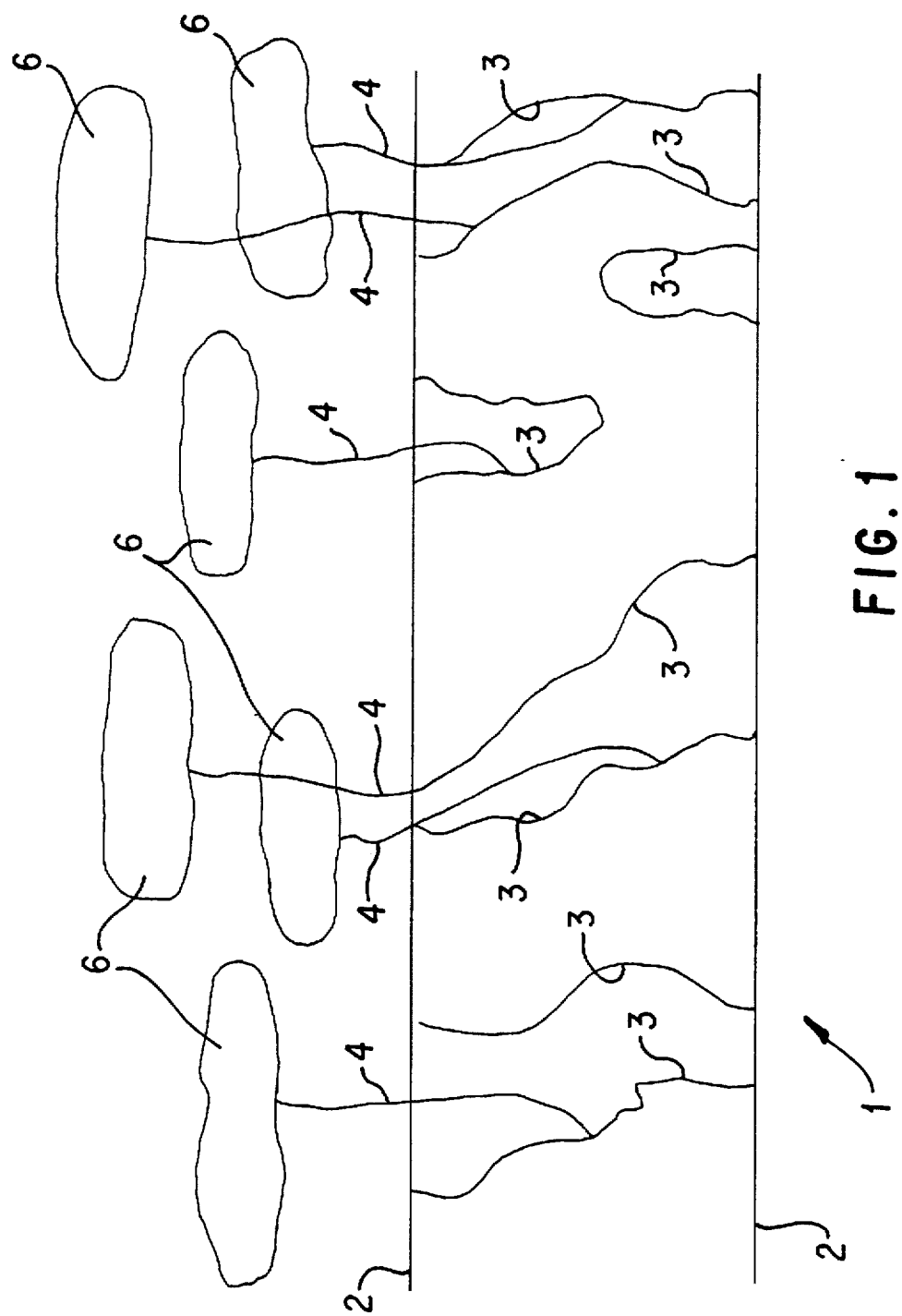

The invention comprises an affinity support for affinity chromatography including an affinity matrix comprising a water-insoluble high flux semipermeable hydrogel membrane supporting highly localized exterior surface concentrations of an affinity ligand extending from the membrane surfaces into the solution interface for maximization of binding capacity of the ligand, particularly for use in immunoaffinity applications. The membrane is selected for pore size (exclusion limit) which permits entry of linking reagents into the interior of the membrane, while restricting entry of the affinity ligand into the membrane. The matrix comprises any affinity matrix as above containing functional groups available for derivatization (activation and linkage to affinity ligand), particularly free hydroxyl or amino groups; exemplary preferred matrices are cellulose, derivatized cellulose, and chitosans and aromatic polyamides, or other membranes which have a suitable NMWCO (see below) and suitable free functional groups, particularly amine or hydroxyl groups. Preferably, the matrix is a hollow-fibre cellulosic membrane containing free hydroxyl groups covalently linked to an affinity protein or other ligand via a spacer molecule and an optional bifunctional linking agent, especially a diepoxide, using an all-aqueous solvent system. The affinity support of the invention is particularly useful for capturing insoluble biological macromolecules unable to penetrate the pores of the membrane, cells, and cell fragments in known affinity chromatography processes.

DETAILED DESCRIPTION OF THE INVENTION

1. The Affinity Matrix.

The matrix of the invention comprises a thin, semipermeable, high-flux, water-insoluble, hydrated hydrogel membrane, having free reactive groups for immobilization of ligand, especially free hydroxyl groups. Exemplary hydrogels include known cellulose, derivatized cellulose, and chitosan matrices. Other water-swellable, water-insoluble polymers such as vinyl alcohol copolymers with, for example, ethylene (available from EVALCA, Pasadena, Tx as EVAL polymers), having hydroxyl or other functional groups available for reaction with the selected linking reagents may be used, providing the membranes fulfill the criteria and functions described herein. Preferred is a cellulosic hollow-fiber membrane or film having a dry wall thickness of from about 6 to about 15 μm, most preferably about $10 \times 10^{-6}$ m. Membranes may have asymmetric or homogeneous structure; when asymmetric membranes are used, the ligand linkage is carried out on the denser surface. Membrane hydraulic permeability is preferably between about 2 ml/min-m²-Hg and 200 ml/min-m²-Hg. Membrane permeability varies with the selected molecular weight cut-off (see below) as known in the art, and cut-offs which decrease the permeability below the above-noted ranges are not recommended if throughflow then decreases to an unsatisfactory level; similarly, cut-offs above these ranges which significantly adversely affect the mechanical strength of the membrane are not recommended. The membrane may be of a substantially flat configuration, capillary tube configuration, or any other useful configuration. The term "cellulosic membrane" refers herein to cellulose or derivatized cellulose membranes which are not fully substituted (i.e., contain sufficient residual hydroxyl groups for covalent linking of a useful amount of ligand, optionally via a spacer molecule, to the membrane), at least about one hydroxyl group per repeating cellobiose unit, particularly regenerated cuprammonium-derived cellulosic membranes which are generally commercially available and have good stability in alkaline solution due to the usually relatively high molecular weight of the starting cellulose. As known in the art, to make films or fibers by the cuprammonium process, the cellulose is dissolved in alkaline solution as a copper complex and regenerated as a hydrogel by shifting the copper equilibrium to precipitate the solid. An alternative method is to dissolve cellulose as its xanthate derivative and to regenerate the product with acid solution, as also known in the art. Other, more recently described solvent systems for regeneration of cellulose to provide membranes useful in the process of the present invention include dimethylacetamide (DMA) containing LiCl or dimethylformamide (DMF) containing nitrosoamine. Any solvent systems providing regenerated cellulosic membranes according to the invention are useful, as long as the relevant physical and chemical properties of the membranes are substantially preserved.

Membranes for use in the practice of the invention further have a nominal (average) molecular weight cutoff (NMWCO) selected for substantial exclusion of affinity ligand from immobilization on interior surfaces (pore/void/channel surfaces) of the membrane. As known, this cutoff or exclusion limit defines the largest molecule which can readily diffuse into the interior membrane structure. The affinity protein or other ligand is thus substantially completely outwardly spaced via direct or indirect (spacer) linkage from the notional exterior surface(s) n of the membrane which form(s) the membrane/solution interface as illustrated in the FIGURE. Depending upon the selected protein or other ligand, general NMWCO limits will typically start at about 100,000 daltons and decrease to smaller limits. A starting NMWCO limit of about 65,000 daltons is exemplary for many proteinaceous ligands, especially antibodies. Again, the preparation of cellulosic and related membranes having a predetermined NMWCO is well-known in the art. As discussed above, the lower NMWCO limit is selected to permit the entry of linking/activating reagent(s) into the interior of the membrane for linkage to free hydroxyl or other functional groups therein, while excluding the selected affinity ligand (paying attention to permeability and mechanical strength considerations, see above). Since the affinity ligands contemplated are macromolecules and the reagents are not, this is readily accomplished. NMWCO differentials between ligand and reagent on the order of magnitude of about 500×are typical.

The notional exterior surface(s) of the affinity matrix (FIGURE) generally also contain(s) free hydroxyl or other functional groups and some of the linking reagents will link to these groups in the course of the linking reactions used to prepare the membrane; the random course of these linking reactions varies with the membrane which varies the outward spacing of the affinity ligand from the notional surface(s) of the membrane has been found to significantly promote density of ligand available for complexing on the exterior surface of the membrane, a known important factor for optimization of affinity separation of the product membrane (see, e.g., *J.Chromatog.* 458:67–77, 1988, p. 68).

2. The Affinity Ligand.

Affinity proteins and other ligands useful for immobilization on the membrane of the invention for affinity chromatography are very well known in the art and do not per se form part of the invention. Exemplary ligands include growth factors, enzymes, enzyme substrates, antigens, and mono- or polyclonal antibodies, especially IgG or IgM. An important group of ligands includes biological molecules or fragments thereof complementary to cell surface receptors or other cell surface determinants; lectin ligands for capture of cells or cell fragments carrying cell surface lectin receptors is exemplary. Immunocapture of antibodies or antigens having binding domains present on intact or fragmented cells from biological solutions, notably blood, by use of complementary affinity ligands is particularly contemplated. Protein ligands may be glycoproteins, or proteins not containing carbohydrate side chains, and the linking mechanisms selected accordingly, as described below. Typical affinity proteins comprise isolated, synthesized, or genetically-engineered optionally modified naturally-occurring proteins, particularly single-chain proteins. Ligands should be selected to minimize irreversible binding with the ligate as known in the art if recovery of the ligate is contemplated.

The term "affinity proteins" as used herein includes protein fragments (polypeptides) having the requisite recognition domains for binding of ligand to ligate, which are often more specific and thus often preferred.

3. Affinity Matrix and Ligand Linkage.

The affinity ligands may be directly or indirectly linked to residual hydroxyl or other functional groups of the matrix membrane by any procedure which substantially retains the mechanical and hydraulic properties of the membrane while substantially retaining the binding activity of the affinity ligand. Typically, as known in the art, matrix free functional groups are activated or modified preparatory to covalent coupling of ligand or the matrix and ligand bridging a spacer molecule to the matrix. The prior art is replete with descriptions of methods for linking various affinity matrices to ligands. Techniques for matrix activation/modification and ligand/spacer coupling as described in *Affinity Chromatography: a practical approach*; Dean, et al. eds.; IRL Press Ltd., P.O. Box 1, Eysham, Oxford OX8 1JJ, England, 1985; and *Affinity Chromatography: Bioselective Adsorption on Inert Matrices*; Elving, et al. eds.; John Wiley and Sons, New York, 1981 are exemplary (both texts are incorporated herein by reference). Many of the procedures for coupling selected ligand to selected matrix described in these texts, or otherwise known in the art are useful in the practice of the invention.

In the present invention, the linkage between matrix and ligand preferably includes a bifunctional spacer agent or "leash" linking the membrane and the affinity protein or other ligand; and more preferably further includes a bifunctional linking reagent linking the membrane and the spacer agent, or the spacer agent and the ligand, or both. The matrix may also, however, be linked to the ligand via the bifunctional linking reagent (omitting the spacer), or be linked directly to the ligand, although these expedients tend to reduce ligand binding capacity owing to stearic hindrance. Also preferably, the linking reaction(s) employed can be accomplished in an all-aqueous solvent system, especially at a pH range of about 4.5 to about 9.5 to minimize aggregation or crosslinking of neighboring immobilized affinity proteins and thus maximize their potential binding capacity.

To immobilize glycoproteins, free vicinal hydroxyl groups may be oxidized to aldehydes and linked to matrix spacer, or linking agent, as known in the art. To immobilize proteins that do not contain carbohydrate groups (non-glycoproteins), various strategies can be employed. For example, an amino acid such as aminocaproic acid can be reacted with the free epoxide group of a diepoxide reagent terminated spacer. This spacer can be activated by any of a number of water-soluble carbodimido compounds for rapid reaction with any amine groups of proteins offered to it.

In exemplary embodiments of the invention,free hydroxyl groups of a cellulosic membrane are linked to a protein ligand such as an antibody via a bifunctional spacer containing at least one terminal primary amino or hydrazido functional group for reaction with the membrane hydroxyl groups. The remaining terminal functional group of the spacer is selected for reaction with free amino or carboxyl functions of a protein ligand, or also with free hydroxyl functions of a glycoprotein ligand. The membrane, spacer, and/or ligand reactive groups are often modified or activated prior to reaction, as known in the art. Convenient spacer molecules for these embodiments include diamines and dihydrazides such as $C_1-C_6$-alkyldiamines and $C_1-C_6$-dihydrazides, and beta-alanine hydrazide, which provide free amino and hydrazido groups for reaction with the ligand, or $C_4-C_6$-alkylamino acids, which provide free carboxyl groups for reaction with ligand.

The terminal amino or hydrazino functions of these spacers are readily coupled to the cellulosic membrane by methods known in the art. For example, membrane vicinal hydroxyl groups may be oxidized, as with periodate followed by an ethylene glycol quench. The resulting aldehyde functions may then be condensed with the terminal amino or hydrazido functions of the spacer to respectively form a Schiff's base or hydrazone linkage with the membrane as illustrated by the following reaction schemes:

Oxidation of Matrix Carbohydrate to form Aldehyde group:

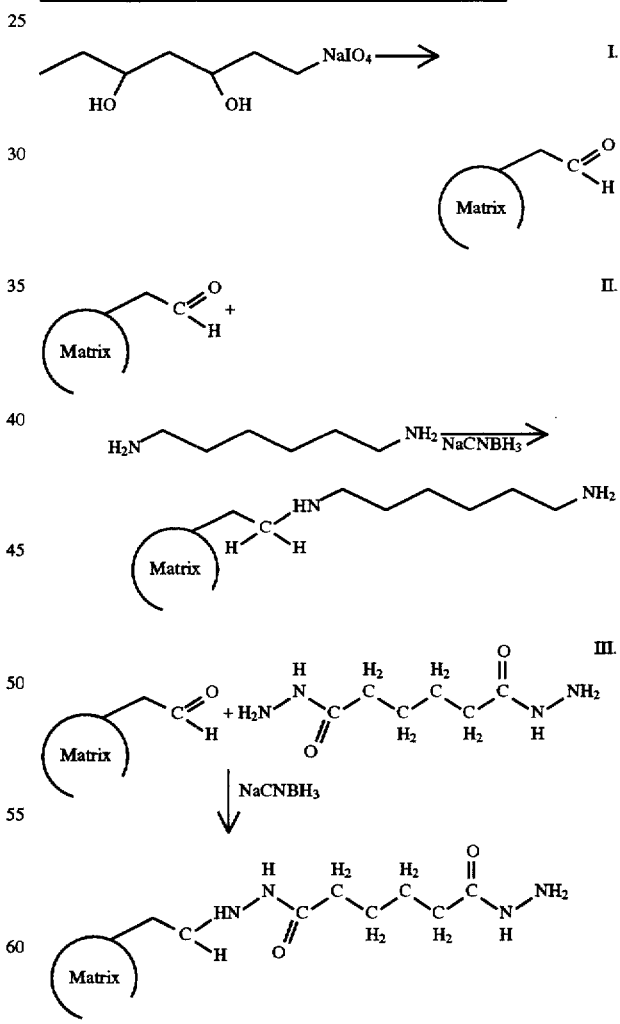

Alternatively, the matrix hydroxyl groups may be activated as known in the art to form active intermediates partially or wholly displaceable by the amino or hydrazido free functional groups of the spacer agents. The use of carbonyldiim-idazole (CDI) in the scheme to form a urethane link with the matrix is exemplary:

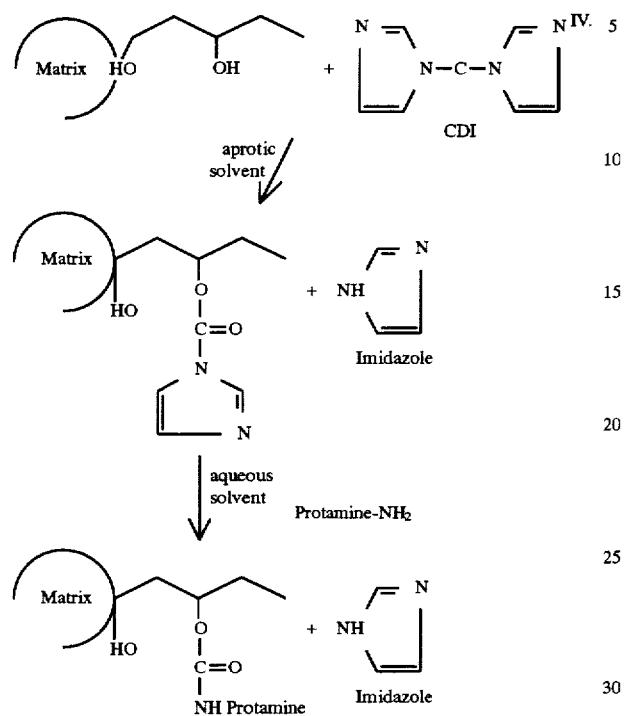

Both these schemes have disadvantages, particularly when used with cellulosic and similar hydrogel membranes. Oxidation of the matrix to provide reactive aldehyde groups tends to adversely affect the mechanical and/or hydraulic properties of the matrix, as does activation with CDI or other activators requiring the use of aprotic solvents.

It is accordingly preferred in the practice of the invention to link the spacer to cellulosic membranes under conditions which do not significantly adversely affect membrane properties. Oxidation of the membrane is avoided by the use of a suitable bifunctional reagent reactive with membrane hydroxyl groups and spacer functional groups under mild conditions for linkage of membrane to spacer. This process also further spaces the ligand away from the membrane and improves exposure of ligand recognition sites to binding complements. Exemplary bifunctional linking reagents for these embodiments include $C_2$-$C_4$-dialdehydes, especially glutaraldehyde, and diepoxides such as $C_2$-$C_4$-diglycidyl ether (EDGDE). In one embodiment, the dialdehyde is reacted with a free hydroxyl group of the membrane to form an acetal linkage, and the remaining aldehyde function is then condensed with an amino- or hydrazido-terminal spacer.

In a particularly preferred embodiment of the invention, a diepoxide is reacted in the presence of an acidic or basic catalyst such as sodium hydroxide with free hydroxyl groups of a cellulosic (cellulose or derivatized cellulose) matrix to form an ether linkage with the matrix while preserving one epoxide function for further reaction with one terminal functional group of a bifunctional spacer. For example, the remaining free epoxy group of the linking reagent may be reacted, as known, with a terminal primary amino or hydrazido group of a spacer also reactive with ligand, such as one of the above-mentioned diamines, dihydrazides or alkylamino acids. This diepoxide route, illustrated in the following reaction schemes, is preferred, as it both avoids oxidation of the membrane and employs an all-aqueous solvent system, thereby preserving membrane strength and hydraulic properties.

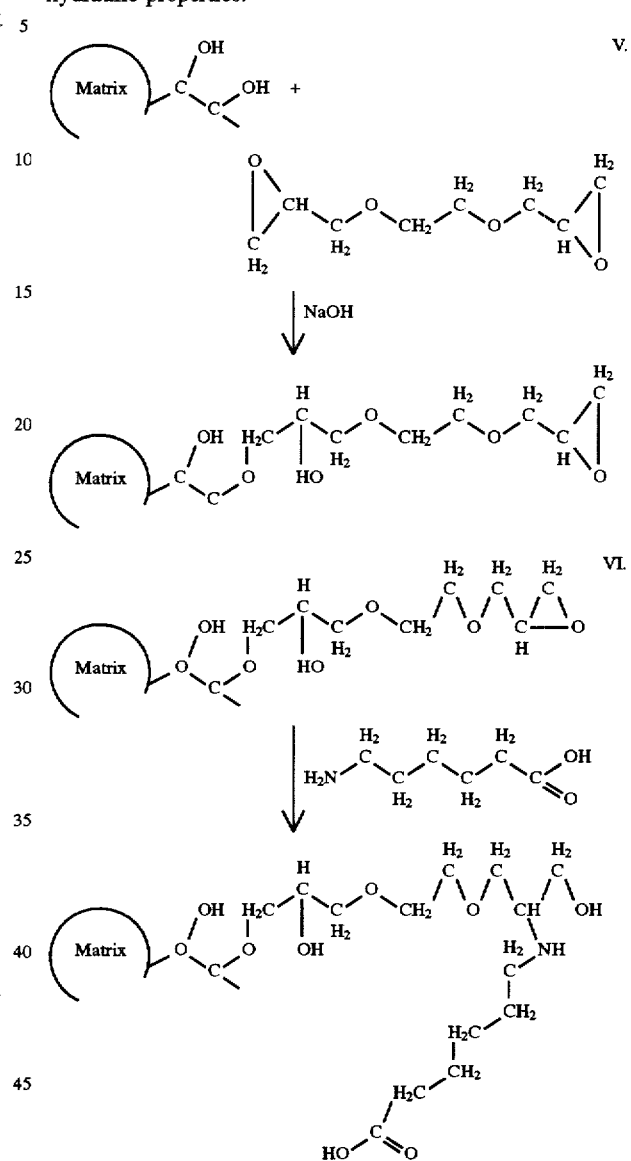

The distal terminal functional groups of the spacer (i.e., the functional groups used for linking spacer to ligand) are selected for reaction with the chosen ligand under conditions which do not significantly compromise ligand biological activity. The spacer, for example, may contain distal terminal leaving groups displaceable by a nucleophilic amino function of some amino acids such as lysine contained in a protein ligand. Distal terminal hydroxyl, amino, or hydrazido groups may be activated as with CDI for reaction with protein primary amino functions to form a urethane or urea link between spacer and protein ligand. Distal terminal amino or hydrazido groups of the spacer may be condensed with oxidized hydroxyl groups of glycoproteins for a Schiff's base or hydrazone linkage, or may be reacted with free carboxyl groups of protein amino acids activated with a water-soluble carbodiimide or other activator. Conversely, distal terminal hydroxyl groups may be oxidized or activated for reaction with protein primary amino groups, and distal terminal carboxyl groups may be activated with, for example, a water-soluble carbodiimide such as ethyldimethylaminopropyl carbodi-imide (EDAC) catalyst for reaction with primary amino functions of ligands, as illustrated in the following reaction scheme:

VII.

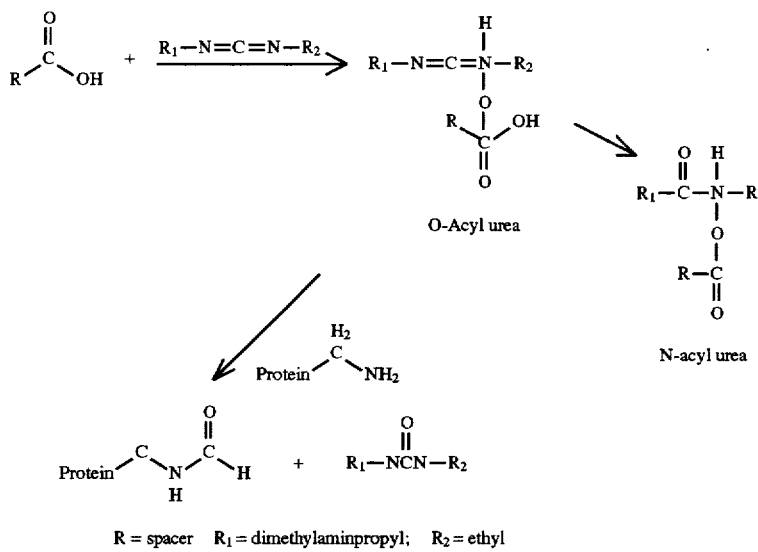

R = spacer   R₁ = dimethylaminpropyl;   R₂ = ethyl

It is preferable to use spacers which can be linked to sensitive ligands such as proteins under mild conditions, which preserve biological activity, particularly by processes employing all-aqueous solvent systems. For glycoprotein ligands, diamine or dihydrazide spacers reactive with diepoxide-modified cellulose and ligand carbohydrate side chains in all-aqueous systems as described above are particularly useful. For both glycoproteins and proteins lacking carbohydrate side chains, CDI-activated diamines or dihydrazides linked to matrix are also useful, as the displacement of the activated groups by protein amino functions takes place in aqueous solvent. For non-glycoproteins, the use of an amino acid spacer linked to an epoxy-modified matrix via the free terminal primary amino group and to ligand by reaction of activated free carboxyl function with ligand amino groups (urea linkage) is particularly convenient.

If desired, a bifunctional linking reagent may also be introduced between the spacer and ligand according to the above-described techniques or otherwise known in the art for facilitating spacer/ligand linkage, or for extending the leash between matrix and ligand.

The ligand may also be directly attached to the matrix, or indirectly attached via a bifunctional linking reagent such as the above-mentioned diepoxides or dialdehydes, also according to the above techniques or those otherwise known in the art.

The sequence of reaction of the matrix, bifunctional linking agent(s), spacer, and ligand is not critical. However, it is usually desirable to attach sensitive ligands in the final step, to avoid the possibility of affecting ligand biological properties in subsequent linking reactions. Other suitable hydrogel matrices with reactive functional groups, especially polyamides having free primary amino functions, may be employed instead of the described cellulosic membranes using the principles of the above-described linking reactions or other reactions known in the art.

Utility

Ligands are preferably immobilized internal to hollow fiber membranes (within the annular space of the hollow fiber (FIGURE) and the fibers disposed in any suitable array for the intended use. Elution of unbound cells can be accomplished as known in the art. Application of shear stress to unbound cells or unbound cell fragments, by for example, increasing viscosity of fluid flowing across the membrane is exemplary; if recovery of bound cells is desired, pretreatment of bound cells as by appropriate enzymes to facilitate elution may be useful.

The following Examples are illustrative of the practice of the invention:

EXAMPLES

Example 1

Activation of Cellulose using CDI, followed by Coupling with either 1,6-Diaminohexane or Aminocaproic Acid to Immobilize Neutrase.

Two modules of cellulose fibers were activated with carbodiimidzole and then with 1,6 diaminohexane or aminocaproic acid to produce a leash from the fiber for the attachment of the Neutrase enzyme. This was done either by utilizing an activated carboxylic acid group on the enzyme to react with the diaminohexane or by using an amine group on the enzyme with the aminocaproic acid. The carboxylic acid group on the enzyme or the one on the aminocaproic acid was reacted with the carbodiimide to form an intermediate for both experiments. For both reactions, the leash on the fiber formed an amide bond with the enzyme. The immobilized enzyme was active in cleaving whey proteins; the latter are too large to enter the membrane matrix, thus demonstrating that the active enzyme was immobilized at the interface of the membrane and the solution Each module was recirculated in 0.1M CDI in acetone for 30 mins. The acetone was removed by blowing air through them for about 15–20 mins. each. A 1% solution of 1,6 diaminohexane or a 1% aminocaproic acid solution was recirculated in each module for 2.5 hours; both solutions were made up in 0.1M bicarbonate buffer pH 8.5. The modules were rinsed with 100mls of buffer and then with DI water. 50 mls of a crude enzyme solution, which had been diluted two times and dialyzed against water, was diluted two times with water and 0.5g carbodiimide added to make a 1% solution. The enzyme was recirculated in each module for one hour. A sample from each enzyme solution was diluted 5 times with mobile phase and 50 ul injected on the HPLC at attenuation 7. A sample of the crude enzyme solution that had been dialyzed, was diluted 10 times with mobile phase and 50 ul injected on the HPLC at attenuation 7 before EDAC addition and water dilution to determine how much enzyme was immobilized. The modules were then assayed for enzyme activity with a whey solution.

Example 2
Activation of Cellulose Modules W/CDI, Aminocaproic Acid and then with BOP Reagent, Triethylamine and N-Hydroxysuccinimide.

This experiment was performed to attach an aminocaproic acid leash and then an n-hydroxysuccinimide group onto the end of the leash. After attachment, trypsin and chymotrypsin were immobilized onto the fibers and tested for enzyme activity using whey proteins. Cleavage of these proteins indicates enzyme activity is located at the interface between the matrix and the bathing solution.

Three cellulose modules were rinsed with 150 mls DI water, and water was exchanged for acetone in 5 step gradients: then, 100 mls of 0.1M CDI in dry acetone were recirculated for one hour at room temperature. The solution was drained and then rinsed with 100 mls dry acetone and the fibers were dried by blowing off the excess acetone with air. The modules were rinsed with 100 mls 0.1M bicarbonate buffer pH 8.5 or at pH 11. Then 0.2M aminocaproic acid in 0.1M bicarbonate buffer was recirculated at pH 8.5 for two modules and pH st 11 for one module.

Water was again exchanged for acetone in the same step gradients described above with the last rinse of dry acetone.

The following solution was the circulated for one hour at room temperature:

- 22 mgs BOP reagent (442g/mol)
- 14 ul triethylamine (19/01.19g/mol)
- 580 mgs n-hydroxysuccinimide (115.1g/mol) in 50 mls dry acetone and a small amount of anhydrous sodium sulfate added to keep solution moisture free The fibers were drained and rinsed with dry acetone and excess removed by blowing air through each module. The module was rinsed with 150mls cold 10mm sodium acetate pH 4.5 and then with 150mls 0.1M borate buffer at pH 8.5. Two solutions of 25 mls of 4mgs/ml trypsin (one for the pH 11 module and the other for the pH 8.5 module) and another 25ml solution of 4mgs/ml chymotrypsin for the pH 8.5 module were recirculated in the cold room for 4 hours. Each module was rinsed with 50 mls 0.1M borate buffer pH 8.5 and then stored in the cold room.

TESTING ACTIVITY OF EACH MODULE

Each column was equilibrated with 0.07M Tris-HCl buffer pH 7.5 At two different flow rates (single pass), 3.75% whey protein solution was continuously pumped through each module and a sample of the effluent collected from each unit after two hours. The sample was diluted 30 times with mobile phase and injected 50 ul at attenuation 4 at 280nm on the TSK gel exclusion column. Another whey sample was also recirculated for two hours through each module. 10mls of 3.75% whey in tris buffer was recirculated and a sample was taken from each solution after one hour and two hours. The samples were prepared the same way as above. The flow rates for each column were tested and the results shown below.

| Module | % area peptide | mgs formed | flow rate mls/min | residence time in module, min | mgs pep/min residence | mgs pep/min residence/ square cm fiber |
|---|---|---|---|---|---|---|
| FOR ONE PASS WHEY THROUGH THE MODULE AT MODERATE FLOW RATE | | | | | | |
| chymotrypsin | 1.3 | 2.44 | 0.138 | 36.23 | 0.967 | 0.000269 |
| trypsin, pH 8.5 | 2.9 | 5.44 | 0.83 | 6.02 | 0.903 | 0.003610 |
| trypsin, pH 11 | 0 | 0.00 | 0.59 | 8.47 | 0.000 | 0 |
| FOR ONE PASS WHEY THROUGH THE MODULE AT SLOW FLOW RATE | | | | | | |
| chymotrypsin | 2.8 | 5.25 | 0.154 | 32.47 | 0.162 | 0.000646 |
| trypsin, pH 8.5 | 9.4 | 17.63 | 0.154 | 32.47 | 0.543 | 0.002171 |
| trypsin, pH 11 | 0 | 0.00 | 0.2 | 25.00 | 0.000 | 0 |

| Module | % area peptide | mgs pep formed | flow rate | residence time in module, min | mgs pep/min residence | mgs pep/min residence/ square cm fiber |
|---|---|---|---|---|---|---|
| RECIRCULATED THROUGH MODULES ONE HOUR: | | | | | | |
| chymotrypsin | 3.1 | 11.63 | 0.154 | 60.00 | 0.194 | 0.000775 |
| trypsin, pH 8.5 | 8.8 | 33.00 | 0.154 | 60.00 | 0.550 | 0.0022 |
| trypsin, pH 11 | 0 | 0.00 | 0.2 | 60.00 | 0.000 | 0 |
| RECIRCULATED THROUGH MODULES TWO HOURS: | | | | | | |
| chymotrypsin | 5.6 | 21.00 | 0.154 | 120.00 | 0.175 | 0.0007 |
| trypsin, pH 8.5 | 17.5 | 65.63 | 0.154 | 120.00 | 0.547 | 0.002187 |
| trypsin, pH 11 | 0 | 0.00 | 0.2 | 120.00 | 0.000 | 0 |

No enzyme activity was observed on the module when pH 11 was used to attach the leash. However, at pH 8.5 all enzymes were active. For both flow rates, moderate and slow, the trypsin with the leash immobilized at pH 8.5 produced peptide at a higher rate than chymotrypsin. For the moderate flow rate, trypsin produced peptide about 9 times as fast as chymotrypsin, 0.903 mgs/min and 0.067 mgs/min respectively. The specific activities were higher at faster single pass flows, perhaps due to reduced product inhibition. When the the product solution was recirculated, these differences vanished. The activities correlate with the available superficial surface areas, indicating the enzyme is located at the interface between membrane and solution

Example 3

Cellulose Modification in Organic Solvent System

The use of carbonyldiimidazole (CDI) for the introduction of an easily replaced "leaving group" is well known in the modification of carbohydrate beads. However, it requires as a first step the dehydration of the carbohydrate since water will rapidly hydrolyze the first imidazole ring from CDI. To effect the dehydration of cellulosic membranes for this modification, organic solvents suitable for condensation of CDI with hydroxyl groups were evaluated. For each solvent the membranes were first exchanged step-wise from water to the pure dry solvent. The CDI/membrane reaction was then carried out by adding 0.1M CDI in the respective solvent for 45 minutes, draining the reaction fluid, and coupling 1,6-hexanediamine to the activated site. The couplings were carried out either in the same solvent ("a" series) or in aqueous buffers ("b" series). Lastly, the fibers were washed, dried and tested for amine content and physical properties. Surprisingly, the most common solvents used in the literature (i.e., acetone, acetonitrile) led to marked loss of mechanical strength. The best solvent system for these activations was found to be DMSO (dimethylsulfoxide) or NMP (N-methylpyrrolidone) as shown by the following data (DMA is dimethylacetaminde):

| Exchange Solvent | Textile Strength | Elongation at Break % |
|---|---|---|
| Control | 47 | 37 |
| DMA-a | 13 | 9.8 |
| DMA-b | 18 | 13.6 |
| Acetone-a | 12 | 5.3 |
| Acetone-b | 13 | 6.8 |
| DMSO | 31 | 49.6 |
| NMP | 28.4 | 46 |

Example 4

Cellulose Fibers Reacted with CDI in 1-Methyl-2-Pyrrolidinone and then 1,6-Diaminohexane in Bicarbonate Buffer In examples 1 and 2 we used acetone as the solvent for dehydrating the cellulose struuucture and as a solvent medium for the CDI reaction. The mechanical properties of the resulting fibers were impaired by the use of this solvent, especially the ultrafiltration coefficients of the resulting membranes. In this example we show that the same chemistry can be achieved in solvents which do not cause these mechanical losses. The solvent n-methyl-pyrrolidinone (NMP) was used for reacting CDI with cellulose. The cellulose fibers were rinsed with water and then exchanged to NMP and equilibrated with dried NMP. 0.1M CDI in NMP was reacted on the fibers for 45 mins. The solution was then drained and a 1% 1,6 diaminohexane solution in 0.1M bicarbonate buffer pH 8.5 was then reacted with the fibers overnight. The solution was then drained and the fibers were rinsed with dilute acid pH 4.0 and then with water. The bundle was split and some was saved for water of imbibition testing and Ninhydrin analysis, some was stored in saline/azide solution and the rest was dried in a solution of 42% glycerol/36% water/22% isopropanol and hung to dry for two days.

Ninhydrin Assay Procedure 0.5–5mgs of cellulose was weighed out and 100ul water was added. A standard curve using L-alanine 0–16ug was used in a total volume of 100ul in water. 500uls of Sigma Ninhydrin Reagent was added to each sample and mixed thoroughly. Each sample was heated for 15 mins. at 100° C. and 2.5mls of 50% n-propanol in water was then added and mixed. Each sample was read at 570nm against the blank without Ala.

Water of Imbibition Procedure

The fibers were rinsed extensively with water and then cut into 1cm pieces. Centrifuged the fibers in capped tubes that split the water from the fibers and kept the fibers in a satu-rated environment of water. Centrifuged at 2000RPM for 10 mins. Fibers were weighed and wet in a tared bottle, dried in the oven and then weighed again. The weight of the water the fibers held was thus obtained.

| | | | RESULTS WATER OF IMBIBITION (WT IN GRAMS) | | | | | | | | | |
|---|---|---|---|---|---|---|---|---|---|---|---|---|
| SAMPLE | WT EMPTY BOTTLE | WT WET FIBERS + BOTTLE | WT DRIED FIBERS + BOTTLE | WT WET FIBERS | WT DRIED FIBERS | WT OF WATER | WATER OF IMBIBITION | WT WATER/ WT FIBERS | Abs 570 | μmoles N | mgs used | μmoles n/ mg fiber |
| NMP1 | 4.6135 | 4.7839 | 4.635 | 0.1704 | 0.0215 | 0.1489 | 0.873826 | 6.925581 | 0.2837 | 0.0470 | 0.382 | 0.122958 |
| NMP2 | 4.6423 | 4.7914 | 4.6606 | 0.1491 | 0.0183 | 0.1308 | 0.877263 | 7.147540 | 1.1555 | 0.1874 | 1.378 | 0.135990 |
| NMP 3 | 4.6591 | 4.9078 | 4.6907 | 0.2487 | 0.0316 | 0.2171 | 0.872939 | 6.870253 | 0.4397 | 0.0721 | 0.444 | 0.162382 |
| NMP 4 | 4.6157 | 4.7645 | 4.6362 | 0.1488 | 0.0205 | 0.1283 | 0.862231 | 6.258536 | 1.7777 | 0.2876 | 2.751 | 0.104549 |
| | | | | | | | AVG. = 0.8747 | AVG. = 6.9811 | | | | AVG. = 0.131470 |

The amount of amine bound to the fiber was 0.13147 umoles/mg fiber. This compares to 0.117798 umoles/mg fiber for the same reaction using CDI in DMA and then 1.6 DAH in water (instead of bicarbonate in this experiment). The results for the water of imbibition walues are shown below for various reaction combinations:

| SAMPLE | WET FIBERS | | |
|---|---|---|---|
|  | UMOLES N/ MG FIBER | WT WATER/ WT FIBER | WATER IMBIBITION |
| CONTROL, NO RXN | 0.00458 | 5.4175 | 0.84405 |
| CDI IN NMP.DAH IN BICARB | 0.13147 | 6.9811 | 0.8747 |
| CDI IN DMA/DAH IN WATER | 0.11779 | 5.303 | 0.84125 |
| CDI IN DMA/DAH IN DMA 0. | 0.19877 | 6.214 | 0.86138 |

The ultrafiltration coefficient is 73.865 ml/hr-sqm-mmHg.

The higher the water of imbibition the more expanded is the structure, and the higher the ultrafiltration coefficient. The starting ultrafiltration coefficient of the control fibers was 137 ml/m$^2$-hr-mm Hg.

| ULTRAFILTRATION MEASUREMENTS | | | | | |
|---|---|---|---|---|---|
| Dp mmHg | t sec | V cc | a sq meter | Q ml/hr | Lp ml/hr-sq m-mmHg |
| 90 | 85 | 0.5 | 0.003486 | 21.18 | 67.478 |
| 161 | 44 | 0.5 | 0.003486 | 40.91 | 72.870 |
| 225 | 31 | 0.5 | 0.003486 | 58.06 | 74.009 |
| 335 | 19 | 0.5 | 0.003486 | 94.74 | 81.101 |
|  |  |  |  |  | AVG. = 73.865 |

The module contains 30 fibers, 20 cm long.

Example 5

Cellulose Reacted with Sodium Meta-Periodate then with Adipic Dihydrazide

This example is based on a procedure from "The Derivatization of Oxidized Polysaccharides for Protein Immobilization and Affinity Chromatography" by E. Junowicz and S. Charm. Biochimica et Biophysica Acta 428 157–165 (1976), using cellulose hollow fibers from Akzo Faser AG (Wuppertal, FRG)and apidic dihydrazide.

Six bundles of cellulose in 10ml glass pipettes were covered with aluminum foil the length of the pipette and 5 cm on either end of the pipette. The bundles were rinsed with deionized water, and then drained. The bundles were reacted with 0.25M Na meta-periodate (26.74g/0.5L) in water for different lengths of time: 15, 30, 45, 60, 75 and 90 minutes. After each length of time, the bundle was drained and rinsed with 60 mls each of di water, 2M NaCl (35.06g/0.3L) and lastly with 70 mls 0.05M Na acetate, pH 4.8 (6.805g/L). The buffer was drained and each module reacted with 60mls 0.15M adipic dihydrazide (15.68g/0.3L) in 0.05M Na acetate pH 4.8 at room temperature overnight. All of the bundles were drained and rinsed with 2L deionized water, then with 60mls 2M NaCl, and finally with 1L DI water. Each bundle was reduced with 60mls of 0.3M Na borohydride (3.4g/0.3L) in 0.1M Tris pH 8.2 (3.63g/0.3L) for two hours at room temperature.

Each solution was drained and rinsed with 1L di water, 60 mls each of 2M NaCl, and then with 2L di water.

Each bundle was split and tested for amine content by ninhydrin reaction.

The rest of the fibers were dried with 36% water/22% isopropanol/42% glycerol by soaking in this solution for four hours and then centrifuging the fibers to get rid of the excess glycerol solution.

| SAMPLE | MGS USED | ABS 570 | UMOLES AMINE | UMOLES/MG FIBER |
|---|---|---|---|---|
| 15 min | 0.663 | 0.299 | 0.0641 | 0.0967 |
|  | 2.232 | 0.7061 | 0.1479 | 0.0663 AVG = 0.0967 |
| 30 min | 0.469 | 0.2849 | 0.0612 | 0.1305 |
|  | 2.473 | 1.3028 | 0.2707 | 0.1095 AVG = 0.1305 |
| 45 min | 0.652 | 0.4577 | 0.0968 | 0.1484 |
|  | 2.319 | 1.0641 | 0.2216 | 0.0955 AVG = 0.1484 |
| 60 min | 0.497 | 0.3299 | 0.0705 | 0.1418 |
|  | 2.147 | 1.6584 | 0.3438 | 0.1602 AVG = 0.1418 |
| 75 min | 0.598 | 0.3058 | 0.0655 | 0.1096 |
|  | 2.393 | 1.2454 | 0.2589 | 0.1082 AVG = 0.1096 |
| 90 min | 0.775 | 0.3749 | 0.0797 | 0.1029 |
|  | 2.587 | 1.3088 | 0.2719 | 0.1051 AVG – 0.1029 |

The fibers after 60, 75 and 90 minutes of reaction felt hard and brittle.The best amount of dihydrazine bound to the fibers with this oxidation-binding-reaction method for 45 minutes is 0.148ug amine/mg fiber. This compares to the results for the binding of 1.6 diaminohexane after CDI activation of 0.131umoles amine/mg fiber. The same amine binding can thus be achieved without using aprotic solvent (CF Example 3).

The experiment was repeated using shorter oxidation times to reduce the mechanical damage due to oxidation. Both the hydrazide end-group concentration and the mechanical properties were measured as a function of oxidation time. While this technique has the advantage of being carried out in aqueous solution—in place of aprotic solvents—it requires a careful balance in the reaction conditions to obtrain adequate hydrazide yield without undue loss of mechanicl properties.

| Oxidation time (min) | umoles NH$_2$/g cell | Tensile Strength (cN) | Elongation at break (%) |
|---|---|---|---|
| 15 | 0.097 | 15.2 | 11.4 |
| 30 | 0.131 | 11.9 | 8.8 |
| 45 | 0.148 | 9.1 | 4.4 |
| 60 | 0.142 | 10.0 | 4.8 |
| 0 | 0 | 31.0 | 46.7 |

While the yield of terminal leash was adequate using this chemistry, there was an unacceptable loss of membrane tensile strength and elongation for reaction times longer than about 30 min.

Example 6

Scale-Up of Protamine Coupled Cellulose hollow Fibers

Protamine-coupled fibers were prepared following the procedure of Example 3. A total of three bundles of RC-HP400 fibers (1000 fibers each bundle) from AKZO Faser AG (Wuppertal, FRG), minus a small amount, were cut to 29 cm in length and placed in a large column (2.3 cm diameter). They were washed with:

| 100% H2O | 2 liters |
|---|---|
| 30% H2O 70% NMP | 1 liter |

| | |
|---|---|
| 100% NMP | 400 ml |
| 100% dry NMP | 400 ml |

NMP = N-methyl pyrrolidinone

The last wash was overnight recirculation with a drying column of anhydrous sodium sulfate in line. The next day 250 ml of 0.1M CDI was recirculated for a total of one hour at room temperature. At the start there was slight foaming possibly due to the moisture in the CDI. The column was drained and washed with 100 ml of dry NMP. 250 ml of 1% protamine (type X) in bicarbonate buffer pH 8.5 was immediately introduced and recirculated two hours at room temperature and over the weekend in the cold room. At the top of the fibers some cloudiness occurred at the beginning but soon after cleared up. The fibers were later washed 3×with 1 liter of D.I. water. 10 cm samples were taken from each of four paired samples and analyzed for protamine using the BCA assay. Afterward the bundle was soaked in glycerin/isopropanol/water (42%/22%/36%), centrifuged and air-dried. The calibration and results are shown in the following table.

later use. Two other modules (C and D) (AKZO) were reacted with 6ml of 1:1 3-aminopropionic acid hydrazide (APAH):D.I. water at room temperature overnight by recirculation. These modules were drained, washed with D.I. water and drained again. These two modules were then stored in the cold room. Two other modules, (E and F) were reacted with 6 ml of 1:1 concentrated $NH_4OH$:D.I. water for one hour at room temperature by recirculation. The modules were drained, washed with D.I. water, drained again, and stored in the cold room.

All four (C thru F) modules were reacted with 3% glutaraldehyde in 0.1M sodium borate buffer, pH 9.4 containing 0.1M $NaCNBH_3$ for one hour at room temperature. The modules were drained, washed with D.I. water, and drained again. 15 ml of 5% protamine in 0.1M borate buffer, pH 9.4 was recirculated for three hours and adjusted to pH of 10.4. The modules were drained, washed with D.I. water, drained again, and stored in the cold room. The next day the modules were reduced with 0.1M $NaCNBH_3$ in 0.1M borate buffer, pH 9.4 for two hours at room temperature, and drained, washed with D.I. water, and drained again. The 3-aminopropionic acid hydrazide modified module yielded 53.0 ug protamine/mg fiber by BCA assay. The ammonia modified fiber yielded 13.0 ug protamine/mg fiber.

| PROTAMINE microgram | ABS | ABS minus blank | REGRESSION | UNKNOWNS-FIBER | BLANK = | |
|---|---|---|---|---|---|---|
| 0 | 0 | 0 | 0.07102 | 0.323 | 0.1056 | 0.2174 |
| 10 | 0.1646 | 0.0951 | 0.11825 | 0.3163 | | 0.2107 |
| 20 | 0.2332 | 0.1637 | 0.16548 | 0.3091 | | 0.2035 |
| 30 | 0.2903 | 0.2208 | 0.21271 | 0.3411 | | 0.2355 |
| 40 | 0.3364 | 0.2669 | 0.25994 | | | |
| 50 | 0.391 | 0.3215 | 0.30717 | | | AVERAGE 0.2168 |
| 60 | 0.4341 | 0.3646 | 0.3544 | | | |
| 70 | 0.4762 | 0.4067 | 0.40163 | | | UNKNOWN |
| 80 | 0.5203 | 0.4508 | 0.44886 | | | 30.86597 micrograms of protamine on 20 cm |
| 90 | 0.5596 | 0.4901 | 0.49609 | | | of fiber |
| 100 | 0.5976 | 0.4281 | 0.54332 | | | 20 cm of fiber = 2.82 mg |
| | | | | | | 30.87 ug/2.82 mg = 10.95 ug Protamine/mg fiber |

| REGRESSION OUTPUT THRU 0 | |
|---|---|
| Constant | 0.07102 |
| Std Err of Y Est | 0.012546 |
| R Squared | 0.993205 |
| No. of Observations | 10 |
| Degrees of Freedom | 8 |
| % Coefficient(s) | 0.004723 |
| Std Err of Coef. | 0.000138 |

Example 7

Protamine-Glutaraldehyde-NH-EGDGE-Cellulose and

Protamine-Glutaraldehyde-APAH-EGDGE-Cellulose

Eight modules were activated. After washing the bore side of the modules with 500ml of D.I. water, the modules were drained. Assuming 2g of water per gram of cellulose, the eight modules had a total of 2.56 grams of water.

We combined:

5 ml of 0.5 M NaOH 20 mg of $NaBH_4$ 5 ml EGDGE (Aldrich)

The modules were connected in parallel, placed in a 50° C. water bath and the above solution was recirculated for one hour followed by extensive washing with D.I. water. Two modules (A and B) were stored in the cold room for Example 8

Protamine-Glutaraldehyde-APAH-EGDGE-Cellulose

Eight of AKZO's Cuprophan mini-modules, were activated after washing the bore and shell sides with 500 ml of D.I. water each and draining. Assuming 2g of water per gram of cellulose, the eight modules had a total of 2.56 gram of water.

We Combined:

5 ml of 0.5 M NaOH 20 mg of $NaBH_4$ 5 ml EGDGE (Aldrich)

The modules were connected in parallel, placed in a 50° C. water bath and the above solution was recirculated for one hour followed by extensive washing with D.I. water. Two modules were reacted with 8 ml of 13% 3-aminopropionic acid hydrazide (APAH) overnight by recirculating at room temperature.

The modules were drained, washed with D.I. water, and drained again. 20 ml of 3% glutaraldehyde in 0.1M borate buffer, pH 9.4 containing 0.1M NaCNBH₃ was recirculated for 30 minutes at room temperature. The modules were drained, washed with D.I. water, and drained again. 20 ml of 1% protamine in bicarbonate buffer, pH 8.5 containing 0.1M NaCNDH₃, and adjusted to pH 10.7 was recirculated for 3 hours at room temperature. The modules were drained, washed with D.I. water, drained again, and stored in the cold room. Solutions of protamine before and after coupling were analyzed by the BCA method, using protamine as the standard.

| ABS UNKNOWNS | UNKNOWNS-BLANK | ug Protamn | cm fiber | ug/cm | ug Protamine/mg fiber |
|---|---|---|---|---|---|
| 0.24817 | 0.16827 | 24.789153 | 4 | 6.1972884 | 77.713997 (not in average) |
| 0.37605 | 0.29615 | 54.684634 | 6 | 9.1141056 | 114.29088 |
| 0.55228 | 0.47238 | 95.883261 | 7.4 | 12.957197 | 162.48325 |
| 0.63737 | 0.55747 | 115.77539 | 10 | 11.577539 | 145.18234 |
| | | | | | AVG = 140.65216 |
| | | | | | STD 19.933524 |

44.9 mg Protamine/module

The average protamine value was found to be 140 microgram/mg fiber.

Example 9

1. Cuprammonium cellulose hollow fibers potted into a plastic housing were washed to remove residual glycerine and then dried with room temperature air. Eight modules (A–H) each containing 1.28g cellulose were perfused with a solution containing 5 ml Of 0.5M NaOH, 20 mg NaBH₄, and 5 ml of ethylene-glycoldiglycydyl ether (EGDGE). The modules (connected in parallel) were perfused with this solution for one hour at 50° C. and then rinsed with deionized water.

a. Two of the modules (A and B) were further modified by reaction with a 1:1 water mixture of 3-amino propionic acid hydrazide for 12 hours to form a leash containing a terminal hydrazide group.

b. Two additional modules (C and D) were reacted with 1:1 dilution of concentrated NH₄OH and water to open the residual epoxy roup and to form an amine terminated leash.

c. The four modules A, B, C, and D were then reacted with 3% glutaraldehyde in 0.1M borate buffer (pH 9.4) containing 0.1M NaCNBH₃ to produce an extended leash on the membrane terminating in an aldehyde group, which is reactive with amine groups of proteins.

d. A protein ligand was then immobilized on the modules A–D from (4) above and the modules E–H from (1) above. In this example the protein used was protamine, a ligand for heparin, a blood anticoagulant. To effect the linkage of the protein a 1% solution of the protein in a pH 10.7 buffer containing 0.1M NaCNBH₃ was used to perfuse the fiber of the modules A–H for 3 hours.

Bound protamine was determined by measuring the protein content of the fibers. On modules A and B the average bound protamine level was 13 mg/g cellulose. On modules E–H, the average bound protein was 5 mg/g of cellulose.

The beneficial effect of the leash can be seen by comparing the yield of immobilized protamine (5 mg/g cellulose) when the protein is reacted directly with the epoxide groups linked to the cellulose (i.e. without intermediate dialdehyde reactions) to the yield of immobilized protamine when the protein is reacted with a hydrazide terminal leash (50 mg/g) cellulose) and an amino terminal leash (13 mg/g cellulose).

Example 10.

An immunoglobulin too large to enter the pore structure of the cellulosic membrane was immobilized, using the leash techniques described above (1a). Cuprammonium derived cellulose hollow fibers were reacted with EGDGE as above then treated with adipic acid dihydrazide (AADH) to produce a hydrazide terminated leash.

a. Separately, 5 ml of anti-human IgG antibody (48 mg) were oxidized with NaIO₄ using known techniques. The antibody was freed of contaminants by a short dialysis and then reacted with the modified fibers.

b. The activity of the immobilized Ab was tested by challenging aliquots of the fiber with increasing concentrations of human-IgG and measuring the mass of Ab bound as a function of the equilibrium concentration. The results were as follows:

| Equilibrium IgG (ug/ml) | Bound IgG (ug IgG/mg fiber |
|---|---|
| 0.426 | 0.091 |
| 0.818 | 0.230 |
| 1.925 | 0.092 |
| 3.810 | 0.239 |
| 7.761 | 0.298 |
| 15.587 | 0.518 |
| 31.574 | 0.532 |
| 63.053 | 1.186 |

What is claimed is:

1. An affinity support for affinity separation including an affinity matrix comprising a high-flux semipermeable hydrogel membrane surface-modified with one or more immobilized affinity ligands, said membrane having free residual functional groups for immobilization of the affinity ligand and pores of a size to provide a nominal molecular weight cutoff small enough to essentially restrict the immobilized ligand outwardly of the exterior surface of the matrix and large enough to permit entry of an immobilizing reagent for ligand immobilization into the interior pores of the membrane for coupling therein, and said immobilized affinity ligand being outwardly spaced from the exterior surface of the membrane and indirectly coupled to a functional group within a pore thereof via the immobilizing reagent wherein one end of the reagent is coupled to the functional group within a pore of the membrane and the other end thereof extends outwardly of the exterior surface of the membrane and is coupled to the ligand.

2. The affinity support of claim 1, wherein the membrane is a cellulosic membrane.

3. The affinity support of claim 2, wherein the membrane is a regenerated cellulose membrane.

4. The affinity support of claim 1, wherein the immobilizing reagent comprises:
   a) a difunctional spacer agent,
   b) a bifunctional linking agent, or
   c) a difunctional spacer agent linked to a bifunctional linking agent;
   said difunctional spacer agent being different from said bifunctional linking agent in a), b) and c).

5. The affinity support of claim 1, wherein the immobilizing reagent comprises a bifunctional linking agent coupled to a difunctional spacer agent different from the bifunctional linking agent, and the bifunctional linking agent is coupled to the functional group in the pore of the membrane.

6. The affinity support of claim 4, wherein the spacer agent is a diamine, dihdrazide, beta-alanine hydrazide, or amino acid.

7. The affinity support of claim 5, wherein the spacer agent is a diamine, dihydrazide, beta-alanine hydrazide, or amino acid.

8. The affinity support of claim 4, wherein the bifunctional linking agent is a diepoxide or a dialdehyde.

9. The affinity support of claim 5, wherein the bifunctional linking agent is a diepoxide or a dialdehyde.

10. The affinity support of claim 4, wherein the bifunctional linking agent is a diepoxide.

11. The affinity support of claim 6, wherein the bifunctional linking agent is a diepoxide.

12. The affinity support of claim 1, wherein the affinity ligand is a protein.

13. The affinity support of claim 12, wherein the protein is a glycoprotein.

14. The affinity support of claim 12, wherein the protein does not contain carbohydrate groups.

15. The affinity support of claim 4, wherein the membrane is a cellulosic membrane and the affinity ligand is a protein.

16. The affinity support of claim 5, wherein the membrane is a cellulosic membrane and the affinity ligand is a protein.

17. The affinity support of claim 6, wherein the membrane is a cellulosic membrane and the affinity ligand is a protein.

18. The affinity support of claim 7, wherein the membrane is a cellulosic membrane and the affinity ligand is a protein.

19. The affinity support of claim 10, wherein the membrane is a cellulosic membrane and the affinity ligand is a protein.

20. The affinity support of claim 11, wherein the membrane is a cellulosic membrane and the affinity ligand is a protein.

21. The affinity support of claim 14, wherein the difunctional spacer agent is a $C_1$–$C_6$-alkylaminoacid.

22. The affinity support of claim 1, wherein the affinity ligand is a complement to a cell surface determinant.

23. The affinity support of claim 22, wherein the affinity ligand is a cell surface receptor.

24. The affinity support of claim 4, wherein the membrane is a cellulosic membrane and the affinity ligand is a cell surface determinant.

25. The affinity support of claim 5, wherein the membrane is a cellulosic membrane and the affinity ligand is a cell surface determinant.

26. The affinity support of claim 6, wherein the membrane is a cellulosic membrane and the affinity ligand is a cell surface determinant.

27. The affinity support of claim 7, wherein the membrane is a cellulosic membrane and the affinity ligand is a cell surface determinant.

28. The affinity support of claim 10, wherein the membrane is a cellulosic membrane and the affinity ligand is a cell surface determinant.

29. The affinity support of claim 11, wherein the membrane is a cellulosic membrane and the affinity ligand is a cell surface determinant.

30. The affinity support of claim 1, wherein the ligand is a complement to a cell surface determinant.

31. A method for the affinity capture of an affinity ligate comprising exposing a solution of ligate to the affinity support of claim 1.

32. The method of claim 31, wherein the ligate is a cell or cell fragment.

33. The method of claim 32, wherein the membrane is a cellulosic membrane.

* * * * *